United States Patent
Eden et al.

(10) Patent No.: US 9,012,209 B2
(45) Date of Patent: Apr. 21, 2015

(54) $CO_2$ OPTICAL SENSOR FOR DETECTION AND ENUMERATION OF MICROORGANISMS

(75) Inventors: Gideon Eden, Ann Arbor, MI (US); Ruth Eden, Ann Arbor, MI (US)

(73) Assignee: Neogen Corporation, Lansing, MI (US)

( * ) Notice: Subject to any disclaimer, the term of this patent is extended or adjusted under 35 U.S.C. 154(b) by 309 days.

(21) Appl. No.: 12/740,078

(22) PCT Filed: Jan. 17, 2008

(86) PCT No.: PCT/US2008/051334
§ 371 (c)(1),
(2), (4) Date: Jun. 10, 2010

(87) PCT Pub. No.: WO2009/091402
PCT Pub. Date: Jul. 23, 2009

(65) Prior Publication Data
US 2010/0273209 A1  Oct. 28, 2010

(51) Int. Cl.
*G01N 21/78* (2006.01)
*B01L 3/00* (2006.01)
(Continued)

(52) U.S. Cl.
CPC ............. *G01N 21/78* (2013.01); *B01L 3/5082* (2013.01); *C12M 41/36* (2013.01); *C12Q 1/06* (2013.01); *G01N 31/22* (2013.01); *B01L 2300/0654* (2013.01); *B01L 2300/0851* (2013.01)

(58) Field of Classification Search
CPC ...... B01L 3/5082; G01N 31/22; G01N 21/78; C12Q 1/06; C12M 41/36
USPC ................................ 435/288.7, 34, 39; 422/73
See application file for complete search history.

(56) References Cited

U.S. PATENT DOCUMENTS

| | | | |
|---|---|---|---|
| 2,992,974 A | 7/1961 | Belcove et al. | |
| 3,756,920 A | 9/1973 | Kelbaugh et al. | |

(Continued)

FOREIGN PATENT DOCUMENTS

| | | |
|---|---|---|
| CA | 2406154 | 4/2004 |
| EP | 0104001 | 3/1984 |

(Continued)

OTHER PUBLICATIONS

International Search Report dated May 20, 2010 from the corresponding International Application No. PCT/US2008/51334 filed on Jan. 17, 2008.

(Continued)

*Primary Examiner* — Nathan Bowers
*Assistant Examiner* — Gautam Prakash
(74) *Attorney, Agent, or Firm* — Honigman Miller Schwartz and Cohn LLP; Noel E. Day; Jonathan P. O'Brien (57) ABSTRACT

A new device and method for detecting the presence of living microorganisms in test samples are described. The device includes a container having at least one section transparent to light with an incubation zone defined in the container, the incubation zone containing growth media in which the sample is cultured. A detection zone containing a matrix composed of a polymeric material which is substantially transparent to light, and at least one indicator reagent sensitive to carbon dioxide gas generated by the microorganisms in the incubation zone is located in the transparent section of the matrix. The matrix is configured to facilitate penetration of external light aimed at the transparent section of the container and interaction of the external light with the indicator reagent to yield interactive light that escapes through the transparent section of the container, said interactive light is being indicative of the presence and/or concentration of the microorganisms.

15 Claims, 5 Drawing Sheets

(51) Int. Cl.
*C12M 1/34* (2006.01)
*G01N 31/22* (2006.01)
*C12Q 1/06* (2006.01)

(56) References Cited

U.S. PATENT DOCUMENTS

| | | | |
|---|---|---|---|
| 3,990,849 A | 11/1976 | Lee et al. | |
| 4,018,652 A | 4/1977 | Lanham et al. | |
| 4,264,728 A * | 4/1981 | Wilkins | 435/287.1 |
| 4,421,849 A | 12/1983 | Breuker | |
| 4,789,804 A | 12/1988 | Karube et al. | |
| 4,803,162 A | 2/1989 | Smith et al. | |
| 4,848,139 A | 7/1989 | Blake-Coleman et al. | |
| 4,945,060 A | 7/1990 | Turner et al. | |
| 5,094,955 A | 3/1992 | Calandra et al. | |
| 5,162,229 A | 11/1992 | Thorpe et al. | |
| 5,164,301 A | 11/1992 | Thompson et al. | |
| 5,164,796 A | 11/1992 | Guiseppi et al. | |
| 5,217,876 A | 6/1993 | Turner et al. | |
| 5,223,402 A | 6/1993 | Abbas et al. | |
| 5,232,839 A | 8/1993 | Eden et al. | |
| 5,266,486 A | 11/1993 | Fraatz et al. | |
| 5,281,537 A | 1/1994 | Robertson et al. | |
| 5,340,747 A | 8/1994 | Eden | |
| 5,366,873 A | 11/1994 | Eden et al. | |
| 5,372,784 A | 12/1994 | Morris et al. | |
| 5,403,741 A | 4/1995 | Holbrook | |
| 5,411,893 A | 5/1995 | Eden et al. | |
| 5,416,002 A | 5/1995 | Steele et al. | |
| 5,529,841 A * | 6/1996 | Neihof | 428/328 |
| 5,672,484 A | 9/1997 | Eden et al. | |
| 5,688,744 A | 11/1997 | Joseph et al. | |
| 5,759,847 A | 6/1998 | Eden et al. | |
| 5,798,214 A | 8/1998 | Squirrell | |
| 5,858,769 A | 1/1999 | DiGuiseppi et al. | |
| 6,085,582 A | 7/2000 | Tripathi et al. | |
| D429,338 S | 8/2000 | Eden | |
| 6,197,576 B1 | 3/2001 | Eden | |
| D457,645 S | 5/2002 | Eden | |
| 6,387,706 B1 | 5/2002 | Eden | |
| 6,395,537 B1 * | 5/2002 | Eden et al. | 435/287.1 |
| 6,605,446 B2 | 8/2003 | Eden | |
| 6,670,174 B1 | 12/2003 | Smith et al. | |
| 6,710,347 B1 | 3/2004 | Eden | |
| 6,855,514 B2 * | 2/2005 | Ogawa | 435/34 |
| 6,979,828 B2 * | 12/2005 | Tokuda | 250/461.2 |
| 7,071,005 B1 | 7/2006 | Eden | |
| D539,434 S | 3/2007 | Eden | |
| 7,558,259 B2 | 7/2009 | Eden | |
| 2002/0026822 A1 | 3/2002 | Reading et al. | |
| 2002/0098531 A1 | 7/2002 | Thacker | |
| 2003/0069795 A1 | 4/2003 | Boyd et al. | |
| 2004/0152150 A1 | 8/2004 | Eden | |
| 2004/0168504 A1 | 9/2004 | Eden et al. | |
| 2004/0200265 A1 | 10/2004 | Eden et al. | |
| 2005/0266516 A1 * | 12/2005 | Kanipayor et al. | 435/34 |
| 2006/0019331 A1 | 1/2006 | Eden | |
| 2007/0008940 A1 | 1/2007 | Eden | |

FOREIGN PATENT DOCUMENTS

| | | |
|---|---|---|
| EP | 0448923 | 10/1991 |
| EP | 0523805 | 1/1993 |
| GB | 2300648 | 11/1996 |
| WO | WO9614429 | 5/1996 |
| WO | WO0039577 | 7/2000 |

OTHER PUBLICATIONS

Written Opinion of the International Searching Authority dated May 20, 2010 from the corresponding International Application No. PCT/US2008/51334 filed on Jan. 17, 2008.

Miyahara et al. "The Conformability of Two Equations for Bacterial Growth in Pork" Czech Journal of Food Sciences, Apr. 2002, v. 20(2) p. 69-73, abstract.

Miyahara et al. "The Conformability of Two Equations for Bacterial Growth in Pork" Chech Journal of Food Sciences, Apr. 2002, v. 20(2) p. 69-73, abstract.

Blackburn et al. "Foodborne Pathogens; Hazards, Risk Analysis and Control," Cambridge: Woodhead Publishing Limited, 2002; 1-521.

Medrala et al. "Application of multiplex PCR in routine microbiological diagnostics of *Listeria monocytogenes* and *Listeria* sp. Strains in a meat-processing plant," Pol. J. Food Nutri. Sci. 2003; 12/53(1):59-64.

* cited by examiner

BAC is Bacillus cereus ATCC 10876
CIT is Citrobacter freundii ATCC 8090
EC is Escherichia coli ATCC 8739
SAT is Staphylococcus aureus ATCC 29737

Fig. 4

ASPNIG is Aspargillus niger ATCC 16404
ASPFOOD is Aspargillus niger isolated from onion
PENNFOOD is Penicillium spp Isolated from gain
ALTFOOD is Alternaria spp.
CONBREAD Is bread contaminated with mold mixture

Fig. 5

CAD is Candida albicans ATCC 10231
SCER is Saccharomyces cerevisiae
PINK is a pink colored Rhodotorula spp.
KLOE is Koleckera spp.

$CO_2$ OPTICAL SENSOR FOR DETECTION AND ENUMERATION OF MICROORGANISMS

BACKGROUND

This invention pertains to methods and devices for the detection and/or enumeration of microorganisms. More particularly this invention pertains to methods and devices for the detection and/or enumeration of microorganisms in opaque and/or highly pigmented products.

The presence and enumeration of microorganisms in industrial samples (food, beverage, dietary supplements, cosmetics, toiletry, etc.) have been traditionally determined by growing the microorganisms in agar in Petri dishes and counting the colonies. In the last two decades, other tests have been practiced for industrial samples. These methods are based on culturing the sample in liquid media and monitoring the metabolites generated during the growth of the microorganisms. Several systems, such as the Bactometer (bioMerieux, Hazelwood, Mo. USA), BacTrak (Sy-Lab, Neupurkersdort, Austria), Malthus Systems (Lab M, Crawley, UK) and the RABIT (Bioscience International, Bethesda, Md. USA), are based on monitoring the electrical properties of the growth media measured via two metallic electrodes immersed in the liquid media. The conductance and capacitance of the electrode-media combination is measured by imposing AC electrical current via the electrodes in the media.

Another practical approach has been developed by the present inventor is described and claimed in U.S. Pat. No. 5,366,873. This approach is particularly suitable for assessing food, dairy, and beverage samples. With this approach, the test container contains two distinct phases: (a) a liquid phase formed from a mixture of growth media and an indicator substrate, and (b) a semi liquid phase, comprising a semi-liquid layer, such as agar, and identical liquid compounds present in the liquid phase. Optical readings are periodically performed to detect the optical transmittance of the semi liquid phase utilizing a light source and a photo detector placed on the opposite sides of the layer. Liquid molecules and ions can quickly diffuse between the two phases which are in equilibrium. The diffusion rate is high, and its consistency makes it adequate for enumeration tests utilizing the following equation:

$$Log(CFU)=A-B \times t_D$$

Wherein CPU is the Colony Forming Units (i.e. the number of microorganisms in the sample). A and B are constants, and $t_D$ is the Detection Time which is the point in time (hours) in which the concentration of the microorganism in the liquid media exceeds a specific threshold (around $10^6$ cells/ml). At this point optical readings through the semi liquid phase start following the exponential growth pattern of the microorganisms.

This device is not without some drawbacks. It cannot measure highly pigmented samples such as colored beverages, gelatin capsules for pharmaceutical and veterinary products, dyes, or blood. During the incubation period the pigments can diffuse into the semi liquid phase and mask the optical readings. Another disadvantage of this device is that the semi-liquid phase (agar) disintegrates in higher temperatures and therefore, the device cannot be thermally sterilized. Consequently, it cannot be used reliably for clinical and sterility tests. Another disadvantage of this device is that the agar occasionally gets dislodged during shipping, particularly when exposed to low and freezing temperatures.

Another practical approach of culturing and monitoring microorganisms (bacteria, yeasts and molds) in test samples in the presence of interfering materials has been developed and successfully commercialized utilizing opaque silicone based optical indicator matrices. One such product has been described by Turner, et al. (U.S. Pat. No. 4,945,060), Calandra, et al. (U.S. Pat. No. 5,094,955), Thorpe, et al. (U.S. Pat. No. 5,162,229), Di Guiseppi, et al. (U.S. Pat. No. 5,164,796), and Turner, et al. (U.S. Pat. No. 5,217,876). The basic principle of this device is to affix a disposable sensor to the interior surface of a transparent container that can monitor the production of $CO_2$ when the microorganisms grow and metabolize. The sensor comprises a solid composition with an optical indicator substrate immobilized within it which is placed Hush against the inside surface of the transparent container, such that the indicator substrate is visible from outside. In this device the sensor is separated from the specimen and its growth media by a solid layer that permits the passage of gas molecules but prevents passage of liquid and particulate matter.

These devices are therefore characterized by two distinctive phases: (a) liquid phase that includes the growth media where the specimen or sample is incubated and (b) solid phase in which the indicator substrate is embedded. Unlike the previous device described in U.S. Pat. No. 5,366,873, no growth media is present in the solid phase and no indicator substrate is present in the media. The solid sensor completely eliminates penetration of liquid and interfering substances including pigmentation molecules, thereby enabling monitoring of highly colored samples.

These devices are slow in reacting to the generation of $CO_2$ by the metabolizing microorganisms. First, the chemical composition of the sensor makes it opaque to light, requiring an instrument that measures optical reflectance. Second, the sensor is placed at the bottom of the container, such that one of its flat surfaces interfaces with the liquid media, while the other surface faces the transparent bottom. The generated $CO_2$ gas has to diffuse along the vertical axis of the sensor until it can vary the optical characteristics of its bottom surface. Since the diffusion rate of the gas in the solid matrix is slow (several hours), the detection of the microorganisms can be severely delayed, which can be critical to patient's life. In addition, the manufacturing process of affixing the sensor to the container and the nature of reflectance optics, result in inherent variability of the optical measurements as related to each device's sensor. Consequently, this sensor is inadequate for enumeration tests and is limited only to presence/absence determinations.

SUMMARY

Disclosed herein is a device for detecting and/or enumerating microorganisms in a sample that is composed of a container having at least one section that is transparent to light. The container includes an incubation zone containing growth media in which the sample is cultured and a detection zone located in the transparent section of the container. The detection zone contains a matrix composed of a crosslinked polymer which is substantially transparent to light, and at least one indicator reagent sensitive to carbon dioxide gas generated by the microorganisms in the incubation zone with the generated carbon dioxide gas diffusing into the matrix in the detection, zone. The matrix of the detection zone is configured to facilitate penetration of external light aimed at the transparent section of the container through the matrix and interaction of the external light with the indicator reagent to yield interactive light that escapes through the transparent section of the container. The interactive light is indicative of the presence and/or concentration of the microorganisms.

Also disclosed is a method of detecting the presence of microorganisms in a sample. The method includes the steps of exposing an indicatory matrix of gas permeable crosslinked polymeric material embedded with an indicator reagent responsive to the presence of carbon dioxide in a culture media containing microorganisms. The method also includes the steps of activating an external light source to generate a light beam directed through the exposed indicator matrix and detecting light from a external light source that has passed through the indicatory matrix; and analyzing said detected light to determine the effect of microorganism generated carbon dioxide on the indicator reagent to determine activity of microorganisms in the culture media.

BRIEF DESCRIPTION OF THE DRAWINGS

The description herein makes reference to the accompanying drawings wherein like reference numerals refer to like parts throughout the several views, and wherein.

DETAILED DESCRIPTION

Disclosed herein is a device and method for optically monitoring and enumerating the growth of microorganisms present in a test sample dispersed in growth media. The device includes a transparent solid matrix composed of a suitable crosslinked polymeric material that changes its optical properties in the presence of carbon dioxide. The change in optical properties is detected by suitable optical transmission measurements of the matrix. Since the microorganisms of interest in the test sample metabolize and generate $CO_2$, monitoring the transparent solid matrix with transmitted light beams can be used to variously a) to determine any or all of the following: the presence or absence of bacterial contamination; b) to enumerate the microorganisms present; c) to provide antimicrobial susceptibility determinations; and d) any combination of the aforementioned.

It is contemplated that the device and method disclosed herein can be used for testing highly pigmented samples such as colored beverages, gelatin capsules, blood samples as well as ascertaining sterility of these and other samples. The device disclosed herein makes use of a transparent silicone material to enable the use of transmitted light to detect and/or enumerate microorganisms rather than utilizing as employed and suggested in various other methods. Since the solid matrix as disclosed herein is formulated to be substantially transparent to light, optical transmittance measurements can be successfully utilized and the inherent variability of reflectance readings eliminated.

Where desired or required, the sensor matrix is placed in a well defined optical window section of the container to avoid the optical variability encountered in various other devices such as that caused by affixing the sensor to the flat bottom of the test container.

Broadly construed, the device disclosed herein is a device for detecting and/or enumerating microorganisms in a sample. It is contemplated that the device can be employed to accomplish any suitable optical or visual method for detecting and/or enumerating microorganisms in a test sample including but not limited to the various methods discussed herein. The microorganisms that can be detected and/or quantified by the device and method disclosed herein include those that can be cultured in suitable growth media and generate a gaseous material such as carbon dioxide as a by product of metabolic processes.

The device includes a container having at least one section that is transparent to light. The container has an interior that defines an incubation zone that contains or can be configured to contain growth media suitable to culture and support microorganisms that are believed to be present. Where desired or required, the growth media employed can be a media that is specific to a desired or target microorganism. It is also contemplated that the growth medium employed can be a non-specific medium. The body of the container also has at least one transparent section and has a detection, zone defined in the interior of the body located in the transparent section. The detection zone contains a matrix composed of a crosslinked polymeric material. The crosslinked polymeric material employed will be one that is substantially transparent to light and can support at least one indicator reagent. The indicator reagent integrated on the matrix material is one that is sensitive to carbon dioxide gas generated by the microorganisms present in the incubation zone (if any), The matrix material of choice is one that will permit diffusion of the generated carbon dioxide gas into the matrix material and into contact with the entrained indicator reagent. As use herein, the term "Crosslinked polymeric material" as used the term is used herein is broadly defined as materials that exhibit at least some degree of crosslinking. Crosslinking can occur due to any mechanism including but not limited to chemical catalysis, heating and other vulcanization processes. Particular materials include various materials which are referred to as "room temperature vulcanizates".

The matrix present in the detection zone is configured to facilitate the penetration of light originating external to transparent region of the through the matrix in a manner that permits the light to interact with the indicator reagent to yield interactive light that escapes through the transparent section of the container and can be observed, recorded and/or quantified. The interactive light is considered to be indicative of the presence and/or concentration of the microorganisms of interest.

Figure 1:
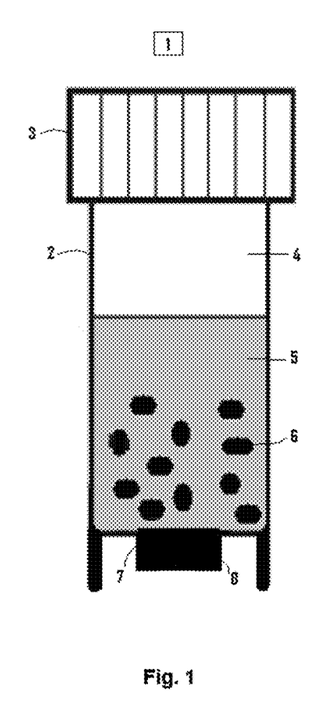
FIG. 1 is a front view of a container included in a device according to an embodiment of the invention as disclosed herein.

A device according to an embodiment of the invention as disclosed herein includes a container 2 as illustrated in FIG. 1 used to incubate a test sample in liquid growth media. The test sample can contain one or more microorganisms for which detection and/or quantification is desired or required. Non-limiting examples of such microorganisms include various bacteria, as well as various yeasts and molds. In certain embodiments of the method and device disclosed herein, it is contemplated that microorganisms detected can include selected groups of organisms, such as *Staphylococcus, E. coli*, and/or lactic acid bacteria.

It is contemplated that the container 2 will have at least one section that is transparent to light. It is contemplated that the container 2 can be composed of any suitable material that is transparent to light. As used herein, the term "transparent to light" is taken to mean transparent to visible light as well as non-visible light in desired spectra. The container can have any suitable size or configuration as desired or required. In the embodiment depicted in FIG. 1, the container 2 can be a plastic vial transparent to light in the visible range and at least a fraction of the long ultraviolet range. One. non-limiting example of a suitable material would be, polycarbonate material can be used which is transparent to the entire visible spectrum and to long ultraviolet radiation above 350 nanometers wavelength. Where desired or required, the material employed will be one that is stable under suitable sterilization procedures. It is contemplated that the material employed will be stable to sterilization at temperatures at or above 121° C.

The container 2 can be sealed with a suitable cap 3 where desired or required. It is contemplated that the cap 3 can be composed, of any suitable material. In the embodiment depicted in FIG 1, the container 2 can be sealed with a cap 3 made of a suitable material such as polycarbonate material. Preferably, both the container 2 and the cap 3 can be thermally sterilized at 121° C, and will remain dimensionally and chemically stable during various sterilization processes.

In the embodiment depicted in FIG. 1, the container 2 includes a suitable detection zone. In various embodiments the detection zone is formed from a suitable optical window 7 containing a suitable indicator matrix 8 and is embedded in the bottom section of (he container 2 forming a detection zone.

In the embodiment as depicted in FIG. 1, the optical window 7 is transparent to light and is formed with 2 parallel opposing surfaces A and B. The container 2 is configured such that the internal volume of the container 2 above the window 7 defines a head space 4, and an incubation zone 5 containing growth media, to which the indicator matrix 8 is exposed.

As shown in FIG. 1, liquid growth media is added into the incubation zone 5 defined in container 2 and comes into contact with the solid indicator matrix 8. The indicator matrix 8, in the embodiment as depicted in FIG. 1, comprises a body of a solid substantially transparent polymer that has an indicator dye dispersed therein. The solid polymer and indicator dye form an optical sensor. Where desired or required, a suitable inorganic base material can be integrated into the polymer to facilitate or augment the action of the entrained indicator reagent material. Non-limiting examples of such bases include potassium hydroxide, sodium hydroxide and the like. Non-limiting examples of suitable indicator reagent materials include Bromocresol green, Methyl red Azolitmin, Bromocresol purple, Bromothymol blue, Phenol red, Thymol blue, Xylenol blue, and the like.

The indicator matrix 8 is composed of a polymeric material that is permeable to gas but totally blocks the passage of any liquid and particulate matter 6 from penetrating into the interior of the matrix body. The incubated microorganisms likewise cannot penetrate from the incubation zone 5 into the indicator matrix 8.

It is contemplated that various polymeric materials can be employed in as the polymeric body of the matrix material provided that the materials are substantially transparent to light and are capable of permitting the diffusion of materials such as carbon dioxide gas through the matrix to the entrained indicator material. As indicated previously, the material of choice will be one that remains chemically and dimensionally stable during sterilization procedures such as temperature treatment at 121° C. Non-limiting, examples of such materials include crosslinked silicone rubber compounds.

The growth media employed in container 2 is one that supports and enables efficient growth of microorganisms originating from the test sample as well as efficient generation of $CO_2$ gas derived from the biological processes of the target microorganisms. Non-limiting examples of several specific and non-specific media can be used, such as Triptic Soy Broth, Plate Count Broth (Difco, Becton Dickenson and Company, Sparks, Md. USA), or CM-Coliform Medium (bioMerieux, Hazelwood, Mo. USA). It is also contemplated that that various types of selective media suitable for the growth of molds and yeast, or selected groups of organisms, such as *Staphylococcus, E. coli*, or lactic acid bacteria can be used where desired or required.

The matrix 8 as disclosed herein is a solid body composed of a suitable crosslinked polymeric material that is substantially transparent to light. The material employed will be one that allows penetration of gases (e.g. $CO_2$.) while preventing optically interfering substances from penetrating. The term "substantially transparent" as the term is used in the disclosure is generally construed as having optical qualities that permit the material to transmit light and enable visual observation and optical readings that are not masked by optical interference resulting from the sample itself and microorganisms turbidity. Materials that are transparent to light, as that term is used herein are materials that, unlike the opaque sensor previously employed in various other sensors that require readings of reflected light from the sensor, can provide responses that can be monitored with transmitted light passing through the full optical path length of the sensor from the surface. A through the surface B of the respective sensor. The transmitted light is not substantially reduced by interfering substances, therefore a high Signal-to-Noise-Ratio signal is obtained following changes in the spectral properties (i.e. color) of the indicator dye embedded in the matrix 8 due to the microbial growth in the incubation zone 5.

Non-limiting exampled of suitable transparent crosslinked or curable polymeric materials include transparent silicone rubbers. Suitable silicon rubber compositions include various RTV silicone rubber compounds specially developed for potting electronic circuits while enabling full visibility of the electronic components. Two non-limiting example of a commercially available silicone rubber composition is ACC Q-Sil 215 and Optitec 7020 manufactured by Adhere, Kidlington, England. While the transparent silicone material itself is transparent, the addition of almost any chemical agent reduces its clarity, especially those agents containing water molecules. The above materials are two-part water clear liquid silicone which cures at room temperature or can be accelerated by heating at around 50° C.

Carbon dioxide is a universal metabolite produced by all microorganisms and therefore can serve as a perfect indicator of microbial growth and metabolism. Since only gases can pass through the silicon-indicator composition and not ions, the $CO_2$ gas generated by microbial metabolism diffuses into the matrix 8 and interacts with the indicator to provide a visual indication of carbon dioxide presence.

In the embodiment disclosed herein, it is contemplated that the material of matrix can also include a suitable mixed base (NaOH or KOH) embedded in the silicon matrix 8. The mixed base can be any suitable material that can be present in an amount sufficient to yield pH lowering material such as carbonic acid ($H_2CO_3$) upon contact with the generated diffused carbon dioxide. The produced carbonic acid, lowers the pH inside the silicone rubber matrix.

It is contemplated that the matrix 8 will also include a suitable indicator reagent. Suitable indicator reagents include pH sensitive dyes such as Bromocresol green, Methyl red, Azolitmin, Bromocresol purple, Bromothymol blue, Phenol red, Thymol blue, Xylenol blue, and the like. These pH indicators and other suitable materials will be those that change their spectral properties (i.e color or fluorescence) as a result of the pH change inside the silicone rubber.

For pH indicators, specific aqueous solutions (buffered KOH or NaOH) are required in addition to the water soluble dye indicator. To enable homogenous dispersion of the dye indicator in the matrix 8, the previous devices described in the prior art, used an emulsion of glycerol with the water-based reagents. This emulsion creates small globules that institute complete opaqueness of the sensor. In-order to maintain the transparency of the polymer, the uncured transparent silicone rubber is embedded with an optimized mixture of an alcohol-based dissolving medium with optimized amount of aqueous solution in quantities sufficient to prevent the presence of globules in the matrix. Care must also be taken not to introduce air bubbles while mixing the viscous material with the reagents, since unreleased tiny air bubbles would also contribute to optical opaqueness after the silicone rubber is cured.

The amount of indicator reagent and base material present in the polymeric matrix will generally be that amount suitable for providing ready evidence or indication of the generation of carbon dioxide by organisms cultured in the associated container. In certain embodiments, it is contemplated that the transparent polymer will be a suitable RTV silicone rubber. In such situations, it is contemplated that the indicator reagent material can be prepared by admixing between a suitable indicator dye material in an amount between 0.01-0.50 grams together with a suitable buffer in amounts between 0.1-3.0 ml with 50 mM buffer and 0.1-3.0 ml 1N base in 2.0-15.0 ml organic liquid. Where desired or required, between 0.05-1.0 ml a suitable dispersion agent such as Tween 80 can also be added to the mixture. The material can be thoroughly admixed and the resulting solution can be added in a suitable proportion to the polymeric matrix prior to cross linking.

Non-limiting examples of indicator dyes that can be employed in the ratios desired include materials such as Thymolphtalein, Bromothymol blue and Xylenol Blue. Non-limiting examples of suitable buffers include materials such as borate and tris-HCI. Suitable base materials include inorganic bases such as NaOH and KOH while the organic liquid can be any suitable alcohol such as ethanol and ethylene glycol as two non-limiting examples.

In various embodiments, it is contemplated that the indicator reagent can be admixed with the resin portion of a suitable silicone rubber material prior to introduction of the cross linking or hardening portion. It is contemplated that between 1.0 to 10.0 ml of the aforementioned indicator reagent can be added to 100 g of the resin portion of a silicone rubber material such as ACC Q-Sil 215. The hardening or curing agent of the polymeric material can be added at an appropriate ratio for the specific polymer employed. The resulting material can be introduced into the containers and allowed to cure for a suitable interval. It is contemplated that the resulting material can cure at room or ambient temperature for an interval of between 10 and 24 hours. Cross-linking can be accelerated by subjecting the material to elevated temperatures of between 35° C and 55° C for an interval of between 0.5 and 2 hours.

Figure 2:
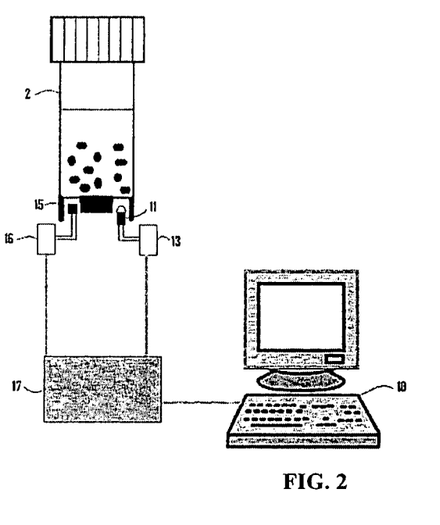
FIG. 2 is a diagrammatic representation of an automated reader setup including a container shown in FIG. 1.

An experimental setup is illustrated in FIGS. 1A and 2 In which the container 2 is combined with optical instrumentation. A visible or ultraviolet light source 11 is located adjacent to surface A of the window 7. The light source 11 may be an incandescent light bulb, light-emitting diode (in the visible or UV range), or gas discharge tube. The light source 11 receives its energy from a suitable source such as an electronic controller 13.

The light passes through the matrix and can be observed or detected by any suitable person or device. In the embodiment depicted in the drawing FIGS. a photo-detector 15 located adjacent to surface B of the window 7 can be used to detect the energy generated by the interaction of the energy from the light source 11 with the matrix 8. The photo-detector 15 can be any suitable device including at least one of a photo diode, photo transistor, photon multiplying tube (PMT), solid state photon counting device or any other light-sensitive device. Where desired or required, the monitoring device can also include a suitable amplifier 16 to amplify the analog signal generated by the photo-detector 15. An electronic processor 17 activates the light source 11 by switching on the controller 13, and processes the analog signal received by the amplifier 16. A computer 18 receives the processed data, stores it in non-volatile memory, and provides real-time analysis of the stored data.

In utilizing the device disclosed herein, it is contemplated that a test sample introduced to the device: may also contain microorganisms. As the microorganisms grow, they produce $CO_2$ gas that can diffuse through the matrix 8 and interact with the basic reagent entrained therein to produce carbonic acid ($H_2CO_3$). The production of carbonic acid causes a drop in the pH affecting the dye indicator reagent also embedded in the matrix 8 to alter the spectral properties of the matrix from an initial state to a reacted state.

The transparent indicator matrix can be prepared in any suitable manner. In at least some embodiments, it is contemplated that the indicator matrix 8 is formed using a high pH solution with a minimal amount of water. The dye or indicator reagent is primarily dissolved in a suitable polar solvent such as an alcohol suitable example-of such materials include ethanol or ethylene glycol. The preparatory solution can also include suitable organic welting agents and/or dispersing agents as desired or required. Non-limiting examples of such material include various Polysorbate detergents. In certain embodiments, it is contemplated that the commercially available materials such as Tween 80 (polyoxyethylene sorbilan monooleate) can be also added in an amount sufficient to achieve dispersion and wetting thereby obtaining an optimized alcohol-water environment.

One advantage of the transparent matrix disclosed herein results from the fact that the light source 11 and the photo-detector 15 can be vertically placed close below the separating line between the liquid in the incubation growth zone 5 and the detection zone. As soon as the generated gas diffuses a short distance into the matrix, the associated color change is immediately detected. Heretofore, opaque matrix necessitated that any gas had to diffuse through the entire thickness of the matrix in order to be able to be detected by reflectance readings at its lowermost surface at the bottom of the test container. It has also been found that the configuration disclosed herein enables effective bacterial enumeration due to the consistency and repeatability of the optical readings. This is further demonstrated in FIG. 6, relative to the reflectance detection technique.

Another advantage of the transparent sensor disclosed herein is its higher sensitivity to microbial growth. In sensors known to this point, whenever $CO_2$ detection was previously required, the test container needed to be a sealable container and the organisms; were cultured after the container was sealed. This generated internal pressure forcing the generated gas to penetrate into the entire volume of the associated matrix. In the device and matrix disclosed herein, the higher sensitivity of the indicator matrix enables gas detection even if the container remains unsealed and is not pressurized by the generated $CO_2$. In this sense, the measurements with the device and method described herein are more reliable because, statistically it can happen that in some instances the test container is not completely sealed, reducing the internal pressure and can therefore result in a false negative determination.

Since the container as disclosed herein need not be sealed, it can also form the basis for antimicrobial susceptibility test devices and Most Probable Numbers (MPN) enumeration devices. In these tests, multiple test containers are required. For example, susceptibility tests can be performed utilizing the convenient format of a micro titer plate with each well containing an indicator matrix affixed to its bottom. Tightly sealing the high number of wells (e.g. 96) is not practical and therefore it is desirable to apply a technique that does not require the sealing step.

In performing analysis using the device as disclosed herein, the sample to be tested is introduced into the container 2 in the incubation zone 5. Where desired or required, the incubation zone can be pre-filled with the suitable liquid growth media. The container is closed with the cap 3, allowing a sufficient volume of air in its head space 4. The container is placed in a; suitable fixture assembly that includes the light source 11 and the photo-diode 15. The fixture assembly is placed into an incubator that is set to optimal temperature for growth of the target microorganisms. In preset time intervals (i.e., 10 minutes), the controller 17 sequentially switches on the light source 11 for a fraction of a second. The photo-detector 15 detects the interactive light resulting from the interaction of the light generated by the light source with the indicator dye embedded in the indicator matrix 8. The signal is amplified by the amplifier 16 and converted to digital data by the processor 17, which also sends it to the computer 18. The data is stored and analyzed during each time interval and can be recorded in any suitable manner

EXAMPLE 1

Sensor and Media Preparation

In order to assess the characteristic of sensors made according to the present disclosure suitable aqueous-based indicator reagent materials are prepared using two different dye indicator materials: Bromothymol blue and Xylenol Blue at different concentrations in the range of 0.01 gms to 0.50 gms. The respective indicator dyes are each admixed with 0.1-3.0 ml of 50 mM buffer (Borate, or Tris-HCl), 0.1-3.0 ml, 1N base (NaOH or KOH), 5.0-15.0ml alcohol (Ethanol, Ethylene Glycol), and 0.05-1.0 ml of Tween 80. The resulting indicator reagents are liquids in which the indicator dye is readily dispersed.

Indicator matrices are prepared by adding the aforementioned reagent indicator material in respective amounts between 1.0-10.0 ml to 100 grams of the silicone resin base portion of a two-part RTV silicone elastomeric composition commercially available under the trade name ACC Q-Sil 215. The silicone resin and the water base dye material are mixed and the curing agent or "B" portion is added per the manufacturer instruction. The resulting silicone elastomer materials with the indicator reagent solution are each dispensed at the bottom of a suitable configured container containing an optical window through which light can pass. A portion of the material samples are allowed, to solidify in various containers overnight at room temperature. Other portions of the materials are allowed to solidify at 55° C for various intervals ranging from 0.5 to 2 hours.

Growth medium containing amino acids and peptides, carbohydrates, minerals, vitamins and other elements known to those skilled in the art to be necessary for the growth of microorganisms in the incubation zone is added to the respective prepared containers. The containers are autoclaved at 121° C. for 15 minutes.

EXAMPLE 2

Utilization of Sensor with Media for the Detection of Bacteria

Containers are prepared with a matrix material as outlined above, the material was allowed to dry overnight at room temperature.

Figure 3:
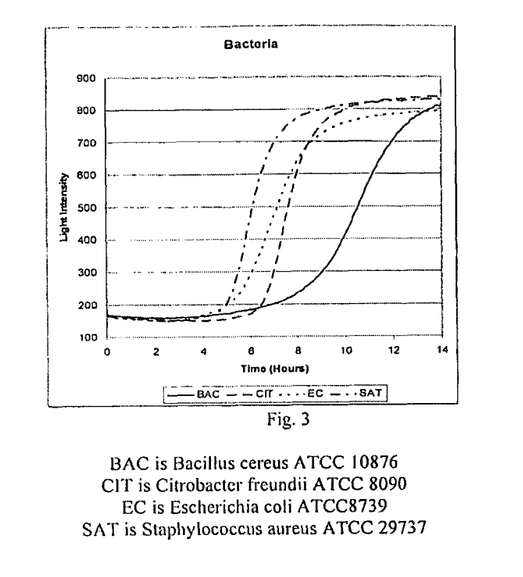
FIG. 3 is a plot of experimental data of bacterial growth obtained by a method performed according to an embodiment of the invention as disclosed herein.

Tryptic soy broth (Difco) enhanced with carbohydrates, vitamins and minerals were added to each container. After autoclave at 121° C. for 15 minutes, the containers are inoculated with various bacteria. FIG. 3 shows the patterns generated due to the bacteria growth in the container. As $CO_2$ is produced by the bacteria the color of the pH indicator changes from dark blue to yellow resulting in an increase in the transmitted light.

EXAMPLE 3

Utilization of Sensor with Media for the Detection of Mold

Figure 4:
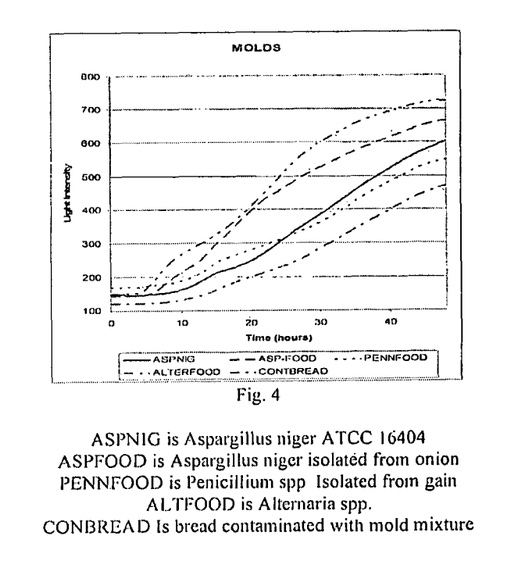
FIG. 4 is a plot of experimental data of mold growth obtained by a method performed according to an embodiment of the invention as disclosed herein.

Tryptic soy broth (Difco) enhanced with carbohydrates, vitamins and minerals; and chloramphenicol (sigma) is added to a container having the silicone-based sensor prepared as above.. After autoclave, the containers are inoculated with various molds. FIG. 4 shows the patterns generated due to the mold growth in the container.

EXAMPLE 4

Utilization of Sensor with Media for the Detection of Yeast

Figure 5:
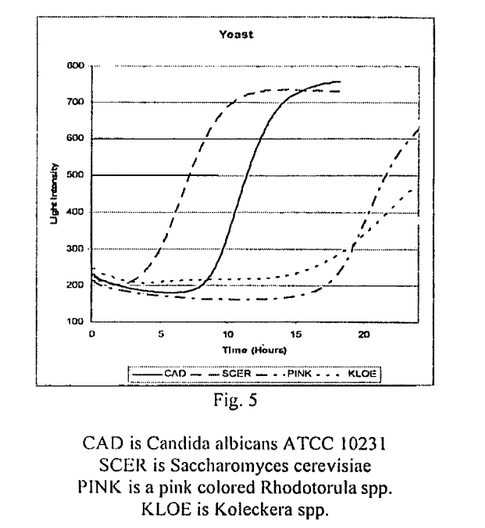
FIG. 5 is a plot of experimental data of yeast growth obtained by a method performed according to an embodiment of the invention as disclosed herein.

Tryptic soy broth (Difco) enhanced with carbohydrates, vitamins and minerals, and chloramphenicol (Sigma) is added to a container having the silicone-based sensor prepared as above. After autoclave, the containers are inoculated with various yeasts. FIG. 5 shows the patterns generated due to the yeast growth in the container.

Mathematical Analysis of Detection Times

It has also been found that the method and device as disclosed herein can be employed to enumerate microorganisms, in a sample rather than merely determining presence/absence. Due to the consistency of the optical readings in the transparent sensor, in high proximity to the liquid media, very repetitive dynamic curves are obtained for identical samples tested in different test containers. In addition, the next mathematical analysis establishes the theoretical basis for the relationship between Detection Time (to) and the microorganism concentration given by the Colony Forming Units (CFU) per ml. This analysis was described in U.S. Pat. No. 5,366,873 for colorimetric measurements. It has been found that the device and method disclosed herein permit the use of this method related to $CO_2$ based metabolic processes. This analysis is followed by experimental data shown in FIG. 6 and FIG. 7 demonstrating that the device and method disclosed, herein is also capable of enumerating microorganisms in contrast to the various methods previously employed in which only presence/absence determinations could be carried out.

When a single strain of microorganisms is introduced to liquid growth media and incubated, there exists an initial phase, defined as the lag phase, in which the microorganisms metabolize but do not significantly multiply, resulting in lag time $t_L$.

During the lag phase, the microorganisms' concentration $C_B$ is:

$$C_B(t) = C_{B0} \ t \leq t_L \quad (1)$$

Where $C_{B0}$ (or CFU) is die initial concentration of the microorganisms.

After the lag phase the logarithmic phase initiates when the microorganisms approximately double every generation time $t_G$. At generation number n, the number of microorganisms is:

$$C_B(n) = C_{B0} \cdot 2^n$$

Taking into account the delay time $t_L$ and that $n=t/t_g$, it follows that:

$$C_B(t) = C_{B0} \cdot e^{(t-t_L) \cdot \ln 2 / t_g} \ t \geq t_L \quad (2)$$

Assuming that each organism generates $K_B$ $CO_2$ gas molecules in the media per unit time, the total number of generated molecules $C_s$ is:

$$C_S(t) = K_B \cdot \int_0^t C_B(t) \, dt \ \phi \geq$$

wherein $K_B$ is defined as the bacterial activity expressed in 1/minute units.

Although during the lag phase microorganisms do not multiply, they are still metabolizing and generating gas molecules. From (1) it follows that;

$$C_S(t) = K_B \cdot \int_0^t C_{B0} \, dt = K_B \cdot C_{B0} \cdot t \ t \leq t_L$$

During the logarithmic phase, the net gas concentration is the sum of its value at the end of the lag phase and the concentration of the molecules generated during the logarithmic phase multiplication. From (1) and (2) it follows that:

$$C_S(t) = K_B \cdot \int_0^{t_L} C_{B0} \, dt + K_B \cdot \int_{t_L}^t C_{B0} \cdot e^{(t-t_L) \cdot \ln 2/t_g} \, dt \quad (3)$$

$$= K_B \cdot C_{B0} \cdot t_L + \frac{K_B \cdot C_{B0} \cdot t_g}{\ln 2} \cdot [e^{(t-t_L)\ln 2/t_g} - 1]$$

$$= K_B \cdot C_{B0} \cdot \left(t_L - \frac{t_g}{\ln 2}\right) + \frac{K_B \cdot C_{B0} \cdot t_g}{\ln 2} \cdot e^{(t-t_L)\ln 2/t_g}$$

The first term in (3) becomes negligible for $t \gg t_L$. Consequently, the total gas concentration increase in time is:

$$C_S(t) = \frac{K_B \cdot C_{B0} \cdot t_g}{\ln 2} \cdot e^{(t-t_L)\ln 2/t_g}$$

At some instant, defined as Detection Time $t_D$, the gas concentration $C_S$ exceeds a threshold amount that the liquid can sustain as soluble gas $C_{SI}$ and the gas molecules diffuse into the sensor and color change takes place. At that instance:

$$C_{SI} = C_S(t) = \frac{K_B \cdot C_{B0} \cdot t_g}{\ln 2} \cdot e^{(t_D-t_L)\ln 2/t_g} \quad (4)$$

and $$t_D = t_L + \frac{t_g}{\ln 2} \cdot \ln \frac{C_{SI} \cdot \ln 2}{K_B \cdot C_{B0} \cdot t_g}$$

Rearranging the terms of (4) and defining $C_{B0}$ as the number of colony forming units CFU we get:

$$CFU = \log^{-1}\left(\log \frac{C_{SI} \cdot \ln 2}{K_B \cdot t_g} - \frac{\log 2}{t_g} \cdot (t_D - t_L)\right) \quad (5)$$

and by combining the intrinsic parameters to empirical coefficients A and B we get:

$$\log(CFU) = A - B \cdot t_D \quad (6)$$

Equation 6 provides a calibration tool by correlating experimental detection times of multiple samples to their Colony Forming Units as measured by standard plating techniques. Applying linear regression analysis to the experimental data, the coefficients A and B can be easily determined.

Figure 6:
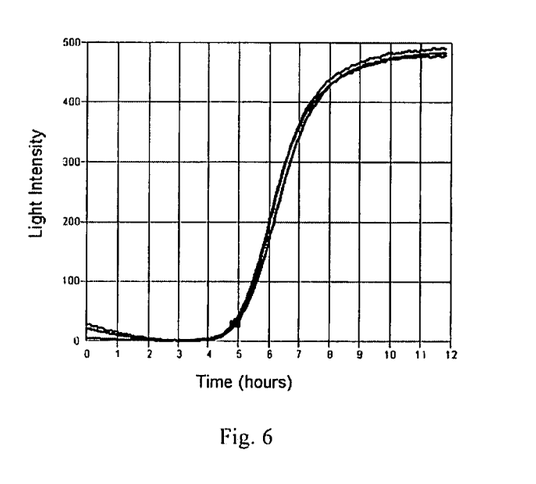
FIG. 6 shows the experimental data of identical samples in different test containers.
Figure 7:
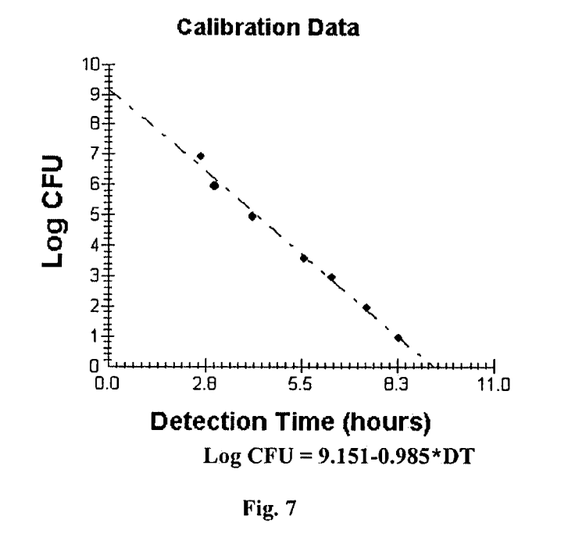
FIG. 7 is an experimental calibration line enumerating Proteus vulgaris bacteria by applying the method performed according to an embodiment of the invention as disclosed herein.

FIG. 6 shows a typical enumeration application of bacteria. A calibration linear curve is obtained by applying the statistical "best fit" algorithms on a scatter gram of experimental data points, each correlating its CFU value with the associated Detection Time. The resulting calibration line is: Log CFU=9.151−0.985*$t_D$ verifying the applicability of Equation (6) above, and establishing the enumeration capability of this invention.

Thus the device as disclosed herein can actually enumerate microorganisms in a sample based on detection times and a calibration line, once its coefficients are experimentally determined. For each assay one can simultaneously obtain the CFU quantity using Petri dishes, along with the Detection Time obtained from the dynamic pattern of the experimental optical readings. This calibration line should be obtained along several bacterial concentrations that are relevant to the practical range obtained from actual test samples.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

We claim:

1. A device for detecting and/or enumerating microorganisms in a specimen, the microorganisms in the specimen generating carbon dioxide gas, the device comprising:
   optical instrumentation, the optical instrumentation including at least one light source unit and a photodetector;
   a container, the container having an outer wall, the outer wall having an upper end and a lower end,
      the container also having a lower floor connected to the lower end of the central wall, the lower floor and the outer wall of the container defining a central chamber,
      the container further having a cell projecting outward and away from the lower floor the central chamber at a location distal to the upper end of the outer wall, the cell communicating with the central chamber, the cell having a first planar wall and a second planar wall each projecting outward from the lower floor of the central chamber, the first and second planar walls disposed in parallel spaced relationship to one another and each having at least one section transparent to light, the cell also has a lower wall disposed contiguously between the first and second planar walls;

an incubation zone defined in the central chamber of the container, the incubation zone containing growth media in which the specimen is cultured;

a detection zone located in the cell defined in the container, the detection zone containing a matrix which is substantially transparent to light and capable of absorbing carbon dioxide gas while substantially preventing liquid and solid penetration into the matrix, wherein the light source unit and the photodetector of the optical instrumentation are positioned external to the cell and the light source produces light that is aimed at the transparent first planar wall of the cell and passes through the matrix present in the detection zone, and at least one indicator reagent disposed in the matrix, the indicator reagent sensitive to carbon dioxide gas that is generated by the microorganisms in the incubation zone and diffuses into the matrix from the incubation zone, wherein the matrix is a silicone rubber, wherein the silicone rubber is substantially transparent to light, the matrix has an upper surface in chemical contact with the liquid growth medium and side surfaces in contact with the first and second planar walls of the cell, and the matrix is configured to facilitate penetration and propagation of the light produced external to the container by the light source, through the matrix, and also configured to facilitate interaction of the propagating light with the indicator reagent present in the matrix to yield interactive light that escapes through the transparent second planar wall at a point that is substantially collinear with the point of external light penetration to the detection zone and contacts the photodetector;

wherein the interactive light is indicative of one of the following: the presence of microorganisms in the specimen, the concentration of microorganisms, in the specimen, or the presence and concentration of microorganisms in the specimen.

2. The device of claim 1, wherein the photodetector is a light sensor capable of measuring the interactive light.

3. The device of claim 2, wherein at least one light source unit located external to the cell is configured to do one of the following:
a) generate visible light and wherein the indicator reagent present in the detection zone is one of a material that registers a color change due to metabolic activity of the microorganisms or a fluorescent dye capable of producing fluorescent light due to the metabolic activity of microorganisms; or
b) generate ultraviolet light and wherein said indicator reagent is capable of producing fluorescent light due to metabolic activity of the organisms.

4. The device of claim 2, wherein the light sensor is one of a photo diode and a photon multiplying tube.

5. The device of claim 2, wherein the light source unit further comprises an optical filter configured to limit electromagnetic energy to specific bands in the light spectrum.

6. The device according to claim 1, wherein said light source unit is at least one of the following: a visible light emitting diode (Vis. LED), an ultraviolet light emitting diode (UV LED).

7. The device of claim 1, wherein:
the light source unit is external to the container,
said external light source is one of the following: a visible light emitting diode (Vis. LED), a laser, or an ultraviolet light emitting diode (UV LED);
the photodetector is a light sensor located external to the container;
the external light sensor is one of the following: a photodiode or a photon multiplying tube (PMT);
and the external light source further comprises an optical filter configured to limit electromagnetic energy to specific spectral bands.

8. The device of claim 7, wherein the matrix is a transparent two-part room temperature vulcanizate silicone rubber.

9. The device of claim 1, wherein the interaction of the propagating light occurs at a location proximate to the upper surface of the matrix and an interface with the incubation zone and the matrix is embedded in the cell thereby providing rapid detection of the diffusing gas.

10. The device of claim 1, wherein the matrix is composed of two-part room temperature vulcanizate silicone rubber,
wherein the silicone rubber is substantially transparent to light; and
the indicator reagent is dispersed in the silicone rubber.

11. The device of claim 1, wherein the cell comprises a cross-linked polymeric material that is transparent to light and dimensionally stable at sterilization temperatures of 121 degrees C.

12. The device of claim 11, wherein the cross-linked polymeric material is a room temperature vulcanizate.

13. The device of claim 12, wherein the matrix further has an opposed lower surface and side surfaces interposed between the upper surface and the lower surface, the lower surface and at least one side surface in adhering contact with a corresponding surface of the cell.

14. A device to enumerate microorganisms in a specimen employing the statistical Most Probable Number (MPN) test, the device comprising:
a plurality of devices as set forth in claim 1, wherein,
in addition to the detection zone and the incubation zone, each of the plurality of devices contain a different dilution of the specimen;
the optical properties of the indicator reagent of each respective device is monitored to determine the presence or absence of the microorganisms in each respective container; and
the containers are unsealed.

15. A device to enumerate microorganisms in a specimen employing the statistical Most Probable Number (MPN) test, the device comprising:
a plurality of devices of claim 1, wherein
the respective containers of the plurality of devices each contain different quantities of a specimen and media mixture;
the optical properties of each indicator reagent is monitored to determine the presence or absence of the microorganisms in each container; and
the containers are unsealed.

* * * * *